(12) United States Patent
Smith et al.

(10) Patent No.: US 12,178,403 B2
(45) Date of Patent: *Dec. 31, 2024

(54) LIGHT FIELD CAPTURE AND RENDERING FOR HEAD-MOUNTED DISPLAYS

(71) Applicant: University of Washington, Seattle, WA (US)

(72) Inventors: Joshua R. Smith, Seattle, WA (US); Samuel R. Browd, Seattle, WA (US); Rufus Griffin Nicoll, Seattle, WA (US); James Andrew Youngquist, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/188,774

(22) Filed: Mar. 23, 2023

(65) Prior Publication Data
US 2024/0000295 A1 Jan. 4, 2024

Related U.S. Application Data

(63) Continuation of application No. 16/463,105, filed as application No. PCT/US2016/063676 on Nov. 24, 2016, now Pat. No. 11,612,307.

(51) Int. Cl.
*A61B 1/00* (2006.01)
*A61B 1/045* (2006.01)
(Continued)

(52) U.S. Cl.
CPC .... *A61B 1/00193* (2013.01); *A61B 1/000095* (2022.02); *A61B 1/00101* (2013.01);
(Continued)

(58) Field of Classification Search
CPC .. H04N 13/344; H04N 13/254; H04N 13/243; H04N 13/282
(Continued)

(56) References Cited

U.S. PATENT DOCUMENTS

| 1,008,973 | A | 11/1911 | Linaweaver |
| 4,383,170 | A | 5/1983 | Takagi |

(Continued)

FOREIGN PATENT DOCUMENTS

| CN | 204854653 U | 12/2015 |
| EP | 1504713 B1 | 7/2008 |

(Continued)

OTHER PUBLICATIONS

US 9,492,073 B2, 11/2016, Tesar (withdrawn)
(Continued)

*Primary Examiner* — Christopher S Kelley
*Assistant Examiner* — Asmamaw G Tarko
(74) *Attorney, Agent, or Firm* — Christensen O'Connor Johnson Kindness PLLC

(57) ABSTRACT

Systems and methods for capturing and rendering light fields for head-mounted displays are disclosed. A mediated-reality visualization system includes a head-mounted display assembly comprising a frame configured to be mounted to a user's head and a display device coupled to the frame. An imaging assembly separate and spaced apart from the head-mounted display assembly is configured to capture light-field data. A computing device in communication with the imaging assembly and the display device is configured to receive light-field data from the imaging assembly and render one or more virtual cameras. Images from the one or more virtual cameras are presented to a user via the display device.

20 Claims, 6 Drawing Sheets

(51) Int. Cl.
*H04N 13/243* (2018.01)
*H04N 13/254* (2018.01)
*H04N 13/282* (2018.01)
*H04N 13/344* (2018.01)

(52) U.S. Cl.
CPC ...... *A61B 1/00181* (2013.01); *A61B 1/00194* (2022.02); *A61B 1/045* (2013.01); *H04N 13/243* (2018.05); *H04N 13/254* (2018.05); *H04N 13/282* (2018.05); *H04N 13/344* (2018.05)

(58) Field of Classification Search
USPC .................................................. 348/48, 159
See application file for complete search history.

(56) References Cited

U.S. PATENT DOCUMENTS

| | | | |
|---|---|---|---|
| 4,694,185 A | 9/1987 | Weiss | |
| 5,757,423 A | 5/1998 | Tanaka | |
| 5,999,840 A | 12/1999 | Grimson | |
| 6,483,535 B1 | 11/2002 | Tamburrino | |
| 6,491,702 B2 | 12/2002 | Heilbrun | |
| 6,577,342 B1 | 6/2003 | Wester | |
| 6,675,040 B1 | 1/2004 | Cosman | |
| 6,985,765 B2 | 1/2006 | Morita | |
| 7,085,409 B2 | 8/2006 | Sawhney et al. | |
| 8,010,177 B2 | 8/2011 | Csavoy et al. | |
| 8,041,089 B2 | 10/2011 | Drumm | |
| 8,218,854 B2 | 7/2012 | Liu et al. | |
| 8,253,797 B1* | 8/2012 | Maali ................ | G06T 7/73 382/113 |
| 8,295,909 B2 | 10/2012 | Goldbach | |
| 8,384,912 B2 | 2/2013 | Charny | |
| 8,548,563 B2 | 10/2013 | Simon | |
| 8,657,809 B2 | 2/2014 | Schoepp | |
| 8,855,408 B2 | 10/2014 | Kim et al. | |
| 8,885,177 B2 | 11/2014 | Ben-Yishai | |
| 8,933,935 B2 | 1/2015 | Yang | |
| 9,119,670 B2 | 9/2015 | Yang | |
| 9,129,377 B2 | 9/2015 | Ciurea et al. | |
| 9,220,570 B2 | 12/2015 | Kim | |
| 9,240,049 B2 | 1/2016 | Ciurea et al. | |
| 9,323,325 B2 | 4/2016 | Perez | |
| 9,361,662 B2 | 6/2016 | Lelescu et al. | |
| 9,462,164 B2 | 10/2016 | Venkataraman | |
| 9,497,380 B1 | 11/2016 | Jannard et al. | |
| 9,503,709 B2 | 11/2016 | Shi et al. | |
| 9,513,113 B2 | 12/2016 | Yang | |
| 9,618,621 B2 | 4/2017 | Barak | |
| 9,629,523 B2* | 4/2017 | Tesar ................ | A61B 50/13 |
| 9,800,856 B2 | 10/2017 | Venkataraman et al. | |
| 9,916,691 B2 | 3/2018 | Takano et al. | |
| 9,918,066 B2 | 3/2018 | Schneider | |
| 9,936,691 B2 | 4/2018 | Gioia | |
| 9,967,475 B2* | 5/2018 | Schneider .......... | G02B 27/0172 |
| 10,074,177 B2 | 9/2018 | Piron | |
| 10,089,737 B2 | 10/2018 | Krieger | |
| 10,165,981 B2 | 1/2019 | Schoepp | |
| 10,166,078 B2 | 1/2019 | Sela | |
| 10,166,079 B2 | 1/2019 | McLachlin | |
| 10,194,131 B2 | 1/2019 | Casas | |
| 10,244,991 B2 | 4/2019 | Shademan | |
| 10,345,582 B2 | 7/2019 | Schneider | |
| 10,353,219 B1* | 7/2019 | Hannaford .......... | H04N 13/366 |
| 10,390,887 B2 | 8/2019 | Bischoff | |
| 10,398,514 B2 | 9/2019 | Ryan | |
| 10,424,118 B2 | 9/2019 | Hannemann | |
| 10,426,345 B2 | 10/2019 | Shekhar | |
| 10,426,554 B2 | 10/2019 | Siewerdsen | |
| 10,433,916 B2 | 10/2019 | Schneider | |
| 10,455,218 B2 | 10/2019 | Venkataraman | |
| 10,546,423 B2 | 1/2020 | Jones | |
| 10,575,906 B2 | 3/2020 | Wu | |
| 10,650,573 B2 | 5/2020 | Youngquist et al. | |
| 10,653,495 B2 | 5/2020 | Gregerson | |
| 10,657,664 B2 | 5/2020 | Yu | |
| 10,667,868 B2 | 6/2020 | Malackowski | |
| 10,682,188 B2 | 6/2020 | Leung | |
| 10,792,110 B2 | 10/2020 | Leung | |
| 10,799,315 B2 | 10/2020 | Leung | |
| 10,799,316 B2 | 10/2020 | Sela | |
| 10,810,799 B2 | 10/2020 | Tepper | |
| 10,828,114 B2 | 11/2020 | Abhari | |
| 10,832,408 B2 | 11/2020 | Srimohanarajah | |
| 10,918,444 B2 | 2/2021 | Stopp | |
| 10,925,465 B2 | 2/2021 | Tully | |
| 10,932,408 B2 | 3/2021 | Chini | |
| 10,949,986 B1 | 3/2021 | Colmenares et al. | |
| 10,973,581 B2 | 4/2021 | Mariampillai | |
| 11,179,218 B2 | 11/2021 | Calef | |
| 11,276,225 B2 | 3/2022 | Youngquist et al. | |
| 11,295,460 B1 | 4/2022 | Aghdasi et al. | |
| 11,354,810 B2 | 6/2022 | Colmenares et al. | |
| 2001/0048732 A1* | 12/2001 | Wilson ................ | A61B 6/4233 378/54 |
| 2002/0065461 A1 | 5/2002 | Cosman | |
| 2002/0075201 A1* | 6/2002 | Sauer ................. | H04N 13/366 348/E13.016 |
| 2002/0082498 A1 | 6/2002 | Wendt et al. | |
| 2003/0011597 A1* | 1/2003 | Oizumi ............... | G06T 15/20 345/427 |
| 2003/0209096 A1 | 11/2003 | Pandey et al. | |
| 2003/0210812 A1 | 11/2003 | Khamene | |
| 2003/0227470 A1* | 12/2003 | Genc ................... | G06F 3/017 345/633 |
| 2004/0169673 A1 | 9/2004 | Crampe | |
| 2005/0070789 A1 | 3/2005 | Aferzon | |
| 2005/0206583 A1 | 9/2005 | Lemelson et al. | |
| 2006/0203959 A1 | 9/2006 | Spartiotis et al. | |
| 2007/0018975 A1* | 1/2007 | Chuanggui .......... | A61B 34/20 345/419 |
| 2007/0121423 A1* | 5/2007 | Rioux ................. | G01V 1/22 367/69 |
| 2008/0004533 A1* | 1/2008 | Jansen ................. | A61B 5/415 600/476 |
| 2009/0303321 A1* | 12/2009 | Olson ................. | H04N 1/053 348/E5.045 |
| 2010/0076306 A1 | 3/2010 | Daigneault | |
| 2010/0099981 A1 | 4/2010 | Fishel | |
| 2010/0295924 A1* | 11/2010 | Miyatani ............ | H04N 13/279 348/46 |
| 2010/0329358 A1 | 12/2010 | Zhang | |
| 2011/0015518 A1 | 1/2011 | Schmidt et al. | |
| 2011/0098553 A1 | 4/2011 | Robbins | |
| 2011/0115886 A1 | 5/2011 | Nguyen et al. | |
| 2012/0027373 A1* | 2/2012 | Chuang .............. | G02B 27/017 386/230 |
| 2012/0050562 A1* | 3/2012 | Perwass .............. | H04N 13/232 348/222.1 |
| 2012/0068913 A1* | 3/2012 | Bar-Zeev ............ | G02B 27/017 345/8 |
| 2013/0002827 A1 | 1/2013 | Lee | |
| 2013/0050432 A1* | 2/2013 | Perez ................. | G06F 3/011 348/47 |
| 2013/0058591 A1 | 3/2013 | Nishiyama | |
| 2013/0222369 A1* | 8/2013 | Huston ............... | G06F 16/954 345/419 |
| 2013/0274596 A1 | 10/2013 | Azizian | |
| 2013/0307855 A1* | 11/2013 | Lamb ................ | G06F 3/013 345/473 |
| 2013/0321925 A1* | 12/2013 | Jacobs .............. | G02B 27/0176 29/428 |
| 2014/0005485 A1* | 1/2014 | Tesar ................. | A61B 17/0293 600/201 |
| 2014/0031668 A1 | 1/2014 | Mobasser et al. | |
| 2014/0092281 A1 | 4/2014 | Nisenzon | |
| 2014/0192187 A1* | 7/2014 | Atwell ............... | G01B 11/25 348/136 |
| 2014/0375772 A1* | 12/2014 | Gabara .............. | H04N 23/661 348/47 |
| 2015/0348580 A1 | 2/2015 | Van Hoff et al. | |

(56) References Cited

U.S. PATENT DOCUMENTS

| | | |
|---|---|---|
| 2015/0173846 A1 | 6/2015 | Schneider |
| 2015/0201176 A1 | 7/2015 | Graziosi et al. |
| 2015/0055929 A1 | 12/2015 | Van Hoff et al. |
| 2016/0073080 A1 | 3/2016 | Wagner |
| 2016/0080734 A1 | 3/2016 | Aguirre-valencia |
| 2016/0091705 A1 | 3/2016 | Ben Ezra et al. |
| 2016/0191887 A1 | 6/2016 | Casas |
| 2016/0217760 A1 | 7/2016 | Chu et al. |
| 2016/0225192 A1 | 8/2016 | Jones |
| 2016/0253809 A1* | 9/2016 | Cole .................. G09G 3/003 345/672 |
| 2016/0307372 A1 | 10/2016 | Pitts et al. |
| 2016/0317035 A1 | 11/2016 | Hendriks et al. |
| 2016/0335475 A1* | 11/2016 | Krenzer ................ G06T 3/40 |
| 2016/0352982 A1 | 12/2016 | Weaver et al. |
| 2017/0007334 A1 | 1/2017 | Crawford et al. |
| 2017/0068081 A1* | 3/2017 | Hirayama .......... A61B 1/00188 |
| 2017/0099479 A1* | 4/2017 | Browd .................. A61B 34/20 |
| 2017/0109931 A1 | 4/2017 | Knorr et al. |
| 2017/0167702 A1 | 6/2017 | Mariampillai |
| 2017/0172670 A1 | 6/2017 | Swarup et al. |
| 2017/0188011 A1 | 6/2017 | Panescu et al. |
| 2017/0200254 A1 | 7/2017 | Kopf et al. |
| 2017/0202626 A1 | 7/2017 | Kula |
| 2017/0237971 A1 | 8/2017 | Pitts |
| 2017/0296293 A1 | 10/2017 | Mak |
| 2017/0318235 A1 | 11/2017 | Schneider et al. |
| 2017/0344121 A1* | 11/2017 | Blanco ................ H04M 1/6066 |
| 2018/0012413 A1 | 1/2018 | Jones et al. |
| 2018/0018827 A1* | 1/2018 | Stafford ................ A63F 13/69 |
| 2018/0070009 A1 | 3/2018 | Baek et al. |
| 2018/0078316 A1 | 3/2018 | Schaewe |
| 2018/0082482 A1* | 3/2018 | Motta ................ G02B 27/0093 |
| 2018/0097867 A1 | 4/2018 | Pang et al. |
| 2018/0239948 A1 | 8/2018 | Rutschman et al. |
| 2018/0262743 A1* | 9/2018 | Casas .................. G06F 3/0304 |
| 2018/0263706 A1 | 9/2018 | Averbuch |
| 2018/0263707 A1 | 9/2018 | Sela et al. |
| 2018/0263710 A1 | 9/2018 | Sakaguchi et al. |
| 2018/0293744 A1 | 10/2018 | Yu |
| 2018/0302572 A1 | 10/2018 | Barnes |
| 2019/0038362 A1 | 2/2019 | Nash |
| 2019/0058870 A1 | 2/2019 | Rowell et al. |
| 2019/0080519 A1* | 3/2019 | Osman ................ H04N 13/383 |
| 2019/0094545 A1 | 3/2019 | Lo et al. |
| 2019/0158799 A1 | 5/2019 | Gao et al. |
| 2019/0158813 A1 | 5/2019 | Rowell et al. |
| 2019/0183584 A1 | 6/2019 | Schneider |
| 2019/0209080 A1 | 7/2019 | Gullotti |
| 2019/0235210 A1 | 8/2019 | Nakai et al. |
| 2019/0260930 A1* | 8/2019 | Van Hoff ............ H04N 13/194 |
| 2019/0282307 A1 | 9/2019 | Azizian |
| 2019/0289284 A1 | 9/2019 | Smith et al. |
| 2019/0290366 A1 | 9/2019 | Pettersson |
| 2019/0328465 A1 | 10/2019 | Li |
| 2019/0336222 A1 | 11/2019 | Schneider |
| 2019/0350658 A1 | 11/2019 | Yang |
| 2020/0005521 A1 | 1/2020 | Youngquist et al. |
| 2020/0059640 A1 | 2/2020 | Browd et al. |
| 2020/0084430 A1 | 3/2020 | Kalarn et al. |
| 2020/0105065 A1 | 4/2020 | Youngquist et al. |
| 2020/0154049 A1 | 5/2020 | Steuart |
| 2020/0170718 A1 | 6/2020 | Peine |
| 2020/0197100 A1 | 6/2020 | Leung |
| 2020/0197102 A1 | 6/2020 | Shekhar |
| 2020/0242755 A1 | 7/2020 | Schneider |
| 2020/0296354 A1 | 9/2020 | Bickerstaff et al. |
| 2020/0297427 A1 | 9/2020 | Cameron |
| 2020/0329226 A1 | 10/2020 | Medal et al. |
| 2020/0342673 A1 | 10/2020 | Lohr et al. |
| 2020/0352651 A1 | 11/2020 | Junio |
| 2020/0405433 A1 | 12/2020 | Sela |
| 2021/0037232 A1 | 2/2021 | Lin et al. |
| 2021/0038340 A1 | 2/2021 | Itkowitz |
| 2021/0045618 A1 | 2/2021 | Stricko, III |
| 2021/0045813 A1 | 2/2021 | Wickham |
| 2021/0077195 A1 | 3/2021 | Saeidi |
| 2021/0145517 A1 | 5/2021 | Pierrepont |
| 2021/0186355 A1 | 6/2021 | Ben-Yishai |
| 2021/0192763 A1 | 6/2021 | Liu |
| 2021/0196385 A1 | 7/2021 | Shelton, IV |
| 2021/0382559 A1 | 12/2021 | Segev |
| 2022/0012954 A1 | 1/2022 | Buharin |
| 2022/0020160 A1 | 1/2022 | Buharin |
| 2022/0174261 A1 | 6/2022 | Hornstein et al. |

FOREIGN PATENT DOCUMENTS

| | | |
|---|---|---|
| EP | 2139419 | 1/2010 |
| EP | 3077956 A4 | 4/2017 |
| EP | 1924197 B1 | 10/2017 |
| EP | 2852326 B1 | 12/2018 |
| EP | 3102141 B1 | 8/2019 |
| EP | 3076892 B1 | 10/2019 |
| EP | 2903551 B1 | 11/2021 |
| EP | 3824621 A4 | 4/2022 |
| IL | 262619 A | 4/2020 |
| WO | 2007115825 A1 | 10/2007 |
| WO | 2008130354 A1 | 10/2008 |
| WO | 2008130355 A1 | 10/2008 |
| WO | 2010067267 A1 | 6/2010 |
| WO | 2014145722 A2 | 9/2014 |
| WO | 2015084462 A1 | 6/2015 |
| WO | 2015151447 A1 | 10/2015 |
| WO | 2015179446 A1 | 11/2015 |
| WO | 2016044934 A1 | 3/2016 |
| WO | 2017042171 A1 | 3/2017 |
| WO | 2018021067 A1 | 2/2018 |
| WO | 2018097831 A1 | 5/2018 |
| WO | 2020018931 A1 | 1/2020 |
| WO | 2020163316 A1 | 8/2020 |
| WO | 2021003401 A1 | 1/2021 |

OTHER PUBLICATIONS

H. Saito, S. Baba and T. Kanade, "Appearance-based virtual view generation from multicamera videos captured in the 3-D room," in IEEE Transactions on Multimedia 5(3):303-316, Sep. 2003.

International Search Report and Written Opinion mailed Jun. 30, 2021, received in corresponding Application No. PCT/US2021/31653, filed May 10, 2021, 17 pages.

* cited by examiner

LIGHT FIELD CAPTURE AND RENDERING FOR HEAD-MOUNTED DISPLAYS

This application is a continuation of U.S. application Ser. No. 16/463,105, filed May 22, 2019, which is a National Stage of International Application No. PCT/US2016/063676, filed Nov. 24, 2016, the disclosure of each of which is expressly incorporated herein by reference in its entirety.

TECHNICAL FIELD

The present technology is generally related to capturing and rendering light fields for head-mounted displays. In particular, several embodiments are directed to light-field capture systems such as an array of cameras and an associated head-mounted display for providing enhanced mediated-reality visualization.

BACKGROUND

Traditional loupes (e.g., surgical loupes) suffer from a number of drawbacks. For example, traditional loupes are customized for each individual, based on the user's corrective vision requirements and interpupillary distance, and so cannot be shared among users. Traditional loupes are also restricted to a single level of magnification, forcing the user to adapt all of her actions to that level of magnification, or to frequently look "outside" the loupes at odd angles to perform actions where magnification is unhelpful or even detrimental. Traditional loupes provide a sharp image only within a very shallow depth of field, while also offering a relatively narrow field of view. Blind spots are another problem, due to the bulky construction of traditional surgical loupes.

One solution involves streaming raw video obtained from two cameras to a head-mounted display (HMD). However, because image capture and image display are inextricably coupled, there are certain limitations in the image data that can be displayed via the HMD. Accordingly, there is a need for improved systems and methods for capturing and rendering stereoscopic image data to a user via a head-mounted display.

DETAILED DESCRIPTION

The present technology is directed to systems and methods for capturing and rendering light fields for enhanced mediated-reality visualization. In one embodiment, for example, a light-field capture device that is spaced apart from a user obtains image data that is then processed and presented to a user stereoscopically via a head-mounted display. As used herein, the term "mediated-reality" refers to the ability to add to, subtract from, or otherwise manipulate the perception of reality through the use of a wearable display. "Mediated reality" display includes at least "virtual reality" as well as "augmented reality" type displays.

Use of relative directional language like top, bottom, front, rear, upper, lower, up, down, upright, upwards, downwards, and others are relative and are not restricted to absolute directions or orientations defined with respect to the surface of the earth.

Specific details of several embodiments of the present technology are described below with reference to FIGS. 1-6. Although many of the embodiments are described below with respect to devices, systems, and methods for capturing and rendering light fields to provide enhanced mediated-reality visualization, other embodiments are within the scope of the present technology. Additionally, other embodiments of the present technology can have different configurations, components, and/or procedures than those described herein. For instance, other embodiments can include additional elements and features beyond those described herein, or other embodiments may not include several of the elements and features shown and described herein. Several embodiments of the present technology can be combined with or can incorporate aspects of the technology disclosed in International Patent Publication No. WO 2015/179446, entitled "Systems and Methods for Mediated-Reality Surgical Visualization," which is hereby incorporated by reference in its entirety.

For ease of reference, throughout this disclosure identical reference numbers are used to identify similar or analogous components or features, but the use of the same reference number does not imply that the parts should be construed to be identical. Indeed, in many examples described herein, the identically numbered parts are distinct in structure and/or function.

Selected Embodiments of Mediated-Reality Visualization Systems

Figure 1:
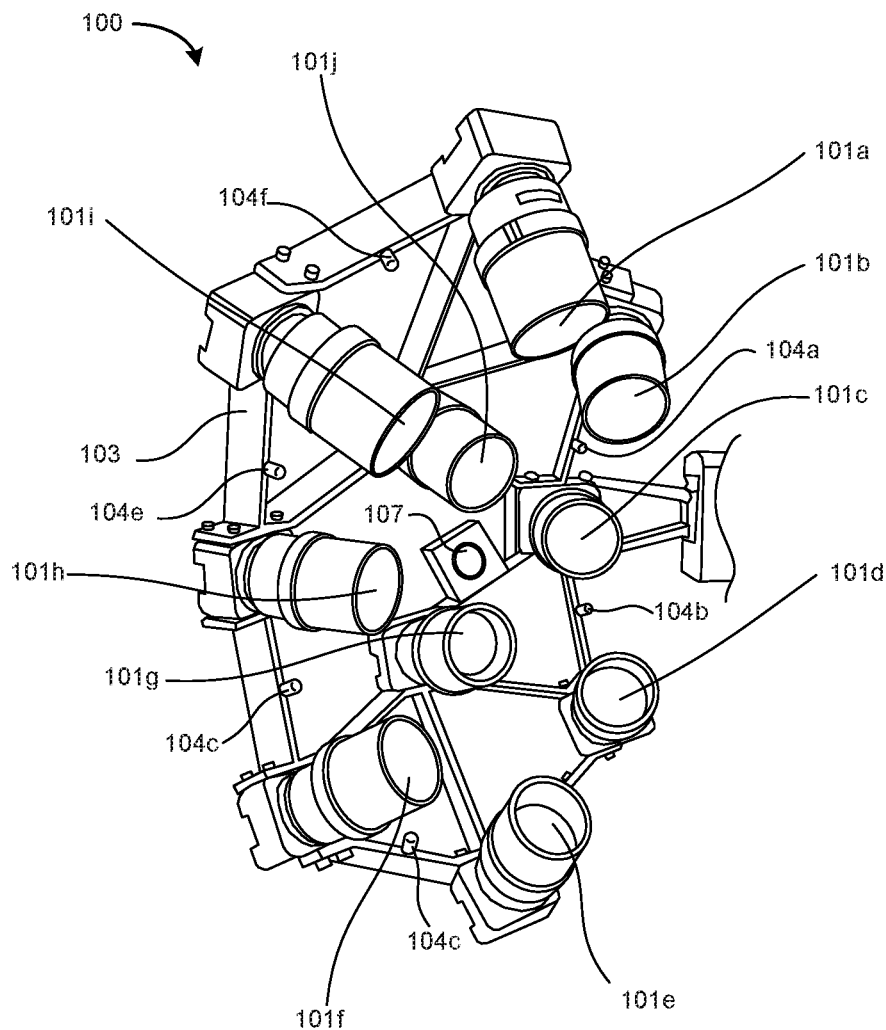
FIG. 1 is a perspective view of an imaging assembly configured in accordance with an embodiment of the present technology.

FIG. 1 is a perspective view of an imaging assembly 100. The imaging assembly 100 includes a plurality of imaging devices 101*a-j* (collectively "imaging devices 101") mounted to a frame 103. In use, the imaging assembly 100 may be positioned close to an object of interest (for example, a surgical site, a workpiece, or other area requiring magnification or otherwise enhanced visualization). The imaging assembly 100 can include mounting armatures as part of the frame 103, which in some embodiments may include mechanisms to change the spacing and orientations of the individual imaging devices 101. The imaging assembly 100 also includes a plurality of light sources 104*a-f* (collectively "light sources 104") that can be selectively activated to enable photometric capture and processing. The imaging assembly 100 also includes at least one projector 107 that can project texture patterns to assist in estimating the geometry of the scene, using multi-view stereo and related techniques. The imaging assembly 100 may be mounted on an articulated arm (not shown) with multiple joints, motors, and encoders for precise positioning and control. By detecting the geometry of the scene, the imaging assembly 100 can be used to render non-planar focal planes such that the entire surface being imaged is in focus, even if the distance between the imaging assembly 100 and different points along the surface varies due to surface topology.

As described in more detail below, information collected by the imaging assembly 100 can be displayed in a head mounted display assembly 200 (FIGS. 2A and 2B), and some features of the imaging assembly 100 and methods may be customized to this head mounted display application. For example, in some embodiments, certain techniques can be used to reduce the data communication requirements of the system, including selectively reading individual imaging devices 101, or selectively reading pixels within each of the imaging devices 101.

The individual imaging devices 101 can be, for example, digital video cameras such as CCD or CMOS image sensor and associated optics. The imaging devices 101 are mounted to a frame 103 and arranged in a semispherical array with the imaging devices 101 directed towards and focused on a common point. However, in other embodiments the imaging devices 101 can be arranged in different configurations, for example a flat array in which the devices do not converge toward a focal point, or even diverge from one another.

The plurality of light sources 105 are disposed around the frame 103 and configured to illuminate the field of view of the imaging assembly 100. The light sources 105 can be, for example, LEDs, fluorescent lamps, or any other suitable illumination source. As described in more detail below, the light sources 105 can be used for photometric geometry estimation and specularity analysis.

The projector 107 can also be attached to the frame 103 and configured to project an image into the field of view of the imaging assembly 100. In one embodiment, the projector 107 is a standard commercially available projector with resolution of 1280×800. In other embodiments, the projector 107 can be any suitable device capable of projecting an image into the field of view of the imaging assembly 100 with a desired resolution. As described in more detail below, the projector 107 can be used to acquire scene geometry information. In some embodiments, the projector 107 can be replaced with one or more light sources and mask optics configured to project fixed texture patterns, which may cost less than the fully dynamic patterns provided by the projector 107.

Although 10 imaging devices 101 are shown, the number of devices used can vary widely. In some embodiments, a single plenoptic camera can be used in place of the array of imaging devices 101. For example, the imaging assembly 100 can include a single image sensor with a lenslet array between the image sensor and the main lens. This lenslet array allows capture of light fields, from which images with different focus planes and different viewpoints (parallax) can be computed. Using light field parallax adjustment techniques, differences in image point of view between the various cameras can be compensated away, so that as the zoom level changes, the point of view does not. The imaging devices 101 can be connected over USB3 or other such connector format to support the high bandwidth data they produce. In one particular embodiment, each imaging device 101 is configured to capture images at 964×964 pixels, at up to 30 frames per second.

As described in more detail below, light-field data captured from the imaging assembly 100 can be rendered to a user stereoscopically, for example via a head-mounted display. In some embodiments, the data captured from the imaging assembly 100 is used to render two "virtual cameras," one positioned at each eye of the user. These virtual cameras can be positioned according to the user's pose based on tracking of the head-mounted display assembly, so that from the user's perspective, she is not wearing a display device at all.

The array of imaging devices 101 allows capture of light-field data such that the imaging assembly 100 can function as a plenoptic camera. Capturing light field data via the imaging assembly 100 and processing the captured light fields is expected to provide several benefits over streaming of direct video or image capture via conventional cameras. For example, light-field rendering enables visual effects that are impossible with physical cameras, such as multiple focal planes (even nonplanar focal surfaces), synthetic apertures, and "seeing through" partial obscuration. And while not impossible for physical cameras, light-field rendering effortlessly enables other useful effects, such as apparently shrinking or growing the user by simultaneously changing the virtual inter-pupillary distance and the distance of the virtual cameras from a scene, which takes advantage of the scale ambiguity in projective geometry. It is through the dynamic scale changes that zoom functionality can be implemented. However, instead of just magnifying an image, the effect can be as though the user is actually shrinking (or the world is growing bigger) with the ability to look around the same scene, but at a closer vantage point.

Figure 2A:
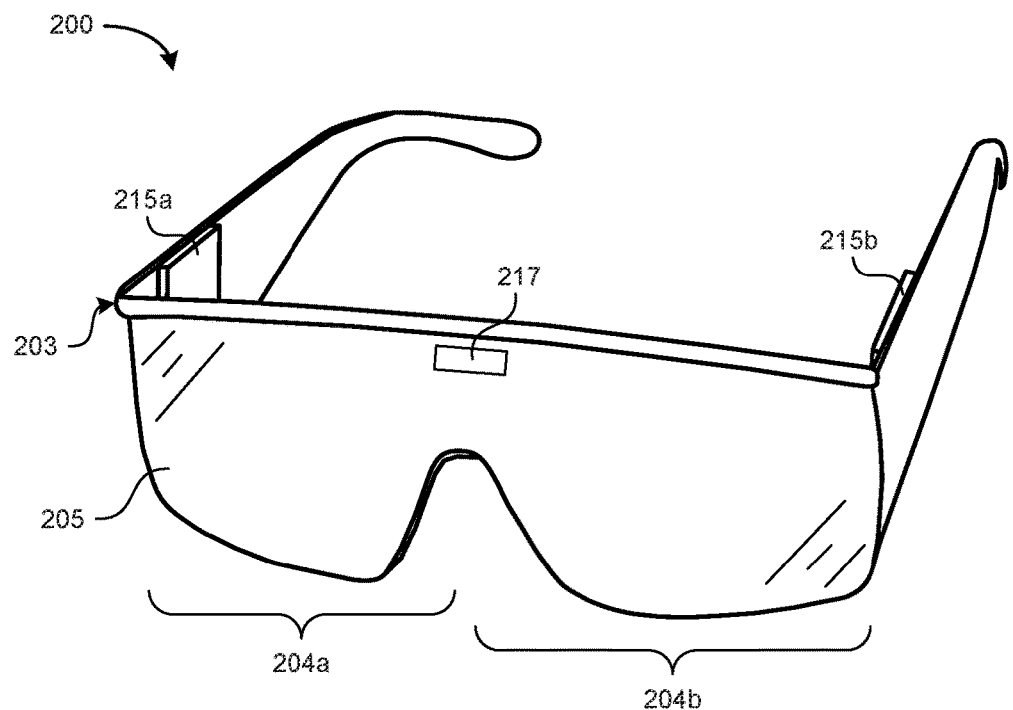
FIGS. 2A and 2B are front and rear perspective views, respectively, of a head-mounted display assembly configured in accordance with an embodiment of the present technology.
Figure 2B:
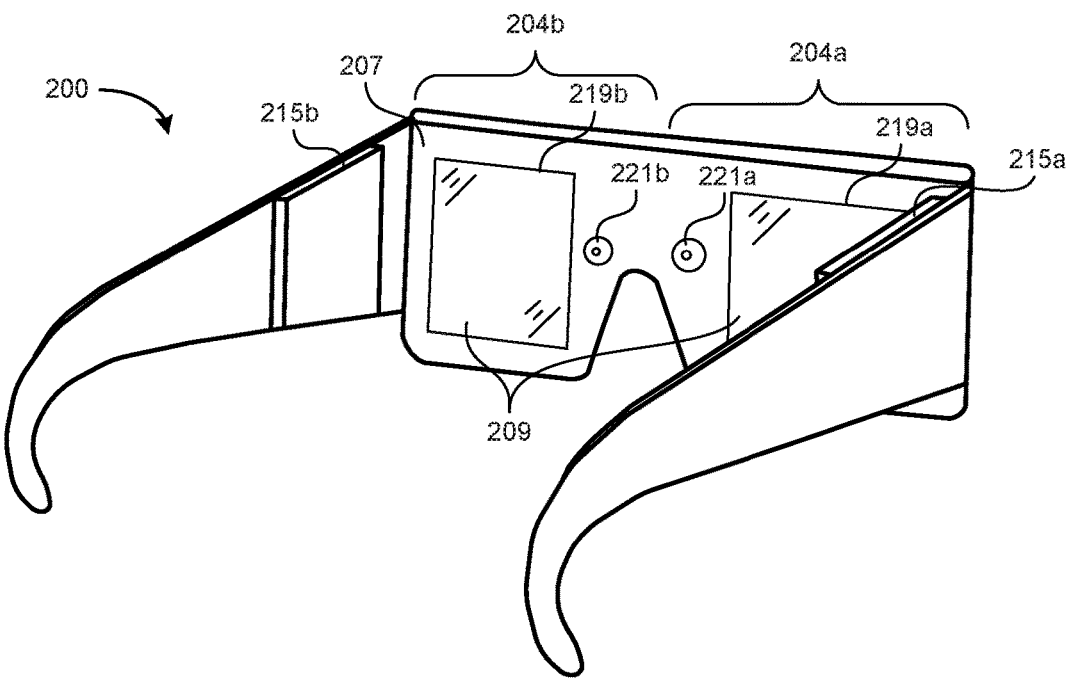

FIGS. 2A and 2B are front and rear perspective views, respectively, of a head-mounted display assembly 200. The display assembly 200 comprises a frame 203 having a forward surface 205 and a rearward surface 207 opposite the forward surface 205. A display device 209 is disposed over the rearward surface 207 and outwardly away from the rearward surface 207. The display assembly 200 is generally configured to be worn over a user's head (not shown), and in particular over a user's eyes such that the display device 209 displays an image towards the user's eyes.

In the illustrated embodiment, the frame 203 is formed generally similar to standard eyewear, with orbitals joined by a bridge and temple arms extending rearwardly to engage a wearer's ears. In other embodiments, however, the frame 203 can assume other forms; for example, a strap can replace the temple arms or, in some embodiments, a partial helmet can be used to mount the display assembly 200 to a wearer's head.

The frame 203 includes a right-eye portion 204a and a left-eye portion 204b. When worn by a user, the right-eye portion 204a is configured to generally be positioned over a users right eye, while the left-eye portion 204b is configured to generally be positioned over a user's left eye. The display assembly 200 can generally be opaque, such that a user wearing the display assembly 200 will be unable to see through the frame 203. In other embodiments, however, the display assembly 200 can be transparent or semitransparent, so that a user can see through the frame 203 while wearing the display assembly 200. The display assembly 200 can be configured to be worn over a user's standard eyeglasses. The display assembly 200 can include tempered glass or other sufficiently sturdy material to meet OSHA regulations for eye protection in the surgical operating room, for example.

The display assembly 200 can include first and second control electronics 215a-b, respectively. The control electronics 215a-b can be configured to provide wired or wireless communication over a network with other components, such as the imaging assembly 100, as described in more detail below with respect to FIG. 3. In the illustrated embodiment, the control electronics 215a-b are coupled to the frame 203. In some embodiments, however, the control electronics 215a-b are coupled to the imaging assembly 100 and communicate wirelessly with the display assembly 200. In other embodiments, the control electronics 215a-b can be integrated into a single component or chip, and in some embodiments the control electronics 215a-b are not physically attached to the frame 203. The control electronics 215a-b can be configured to receive data output from the imaging assembly 100, and can also be configured to control operation of the imaging assembly 100 (e.g., to initiate imaging, to control a physical zoom, autofocus, and/or to operate an integrated lighting source). In some embodiments, the control electronics 215a-b can be configured to process the data output from the imaging assembly 100, for example, to provide a digital zoom, to autofocus, and to adjust image parameters such as saturation, brightness, etc. In other embodiments, image processing can be performed on external devices and communicated to the control electronics 215a-b via a wired or wireless communication link. As described in more detail below, output from the imaging assembly 100 can be processed to integrate additional data such as pre-existing images (e.g., X-ray images, fluoroscopy, MRI or CT scans, anatomical diagram data, etc.), other images being simultaneously captured (e.g., by endoscopes or other images disposed around the surgical site), patient vital data, etc. Additionally, further manipulation can allow for selective enlargement of regions within the field of view.

A fiducial marker 217 can be disposed over the forward surface 205 of the frame 203. The fiducial marker 217 can be used for motion tracking of the display assembly 200. In some embodiments, for example, the fiducial marker 217 can be one or more infrared light sources that are detected by an infrared-light camera system. In other embodiments, the fiducial marker 217 can be a magnetic or electromagnetic probe, a reflective element, or any other component that can be used to track the position of the display assembly 200 in space. The fiducial marker 217 can include or be coupled to an internal compass and/or accelerometer for tracking movement and orientation of the display assembly 200.

On the rearward surface 207 of the frame 203, a display device 209 is disposed and faces rearwardly. As best seen in FIG. 2B, the display device 209 includes first and second displays 219a-b. The displays 219a-b can include, for example, LCD screens, holographic displays, plasma screens, projection displays, or any other kind of display having a relatively thin form factor that can be used in a heads-up display environment. The first display 219a is disposed within the right-eye portion 204a of the frame 203, while the second display 219b is disposed within the left-eye portion 204b of the frame 203. The first and second displays 219a-b are oriented rearwardly such that when the display assembly 200 is worn by a user, the first and second displays 219a-b are viewable by the user with the user's right and left eyes, respectively. The use of a separate display for each eye allows for stereoscopic display. Stereoscopic display involves presenting slightly different 2-dimensional images separately to the left eye and the right eye. Because of the offset between the two images, the user perceives 3-dimensional depth.

The first and second displays 219a-b can be electrically coupled to the first and second control electronics 215a-b, respectively. The control electronics 215a-b can be configured to provide input to and to control operation of the displays 219a-b. The control electronics 215a-b can be configured to provide a display input to the displays 219a-b, for example, processed image data that has been obtained from the imaging assembly 100. For example, in one embodiment image data from the imaging assembly 100 is communicated to the first display 219a via the first control electronics 215a, and similarly, image data from the imaging assembly 100 is communicated to the second display 219b via the second control electronics 215b. Depending on the position and configuration of the imaging assembly 100 and the displays 219a-b, the user can be presented with a stereoscopic image that mimics the perspective that the user would see without wearing the display assembly 200. In some embodiments, the image data obtained from the imaging assembly 100 can be processed, for example, digitally zoomed, so that the user is presented with a zoomed view via the displays 219a-b.

First and second eye trackers 221a-b are disposed over the rearward surface of the frame 203, adjacent to the first and second displays 219a-b. The first eye tracker 221a can be positioned within the right-eye portion 204a of the frame 203, and can be oriented and configured to track the movement of a users right eye while a user wears the display assembly 200. Similarly, the second eye tracker 221b can be positioned within the left-eye portion 204b of the frame 203, and can be oriented and configured to track the movement of a user's left eye while a user wears the display assembly 200. The first and second eye trackers 221a-b can be configured to determine movement of a users eyes and can communicate electronically with the control electronics 215a-b. In some embodiments, the users eye movement can be used to provide input control to the control electronics 215a-b. For example, a visual menu can be overlaid over a portion of the image displayed to the user via the displays 219a-b. A user can indicate selection of an item from the menu by focusing her eyes on that item. Eye trackers 221a-b can determine the item that the user is focusing on, and can provide this indication of item selection to the control electronics 215a-b. For example, this feature allows a user to control the level of zoom applied to particular images. In some embodiments, a microphone or physical button(s) can be present on the display assembly 200, and can receive user input either via spoken commands or physical contact with buttons. In other embodiments other forms of input can be used, such as gesture recognition via the imaging assembly 100, assistant control, etc.

The technology described herein may be applied to endoscope systems. For example, rather than mounting the multiple cameras (with different field or view/magnification combinations) on the imaging assembly 100, the multiple cameras may be mounted on the tip of the endoscopic instrument. Alternatively, a single main lens plus a lenslet array may be mounted on the tip of the endoscopic instrument. Then light field rendering techniques such as refocusing, rendering stereo images from two different perspectives, or zooming may be applied. In such cases, the collected images may be displayed through the wearable head-mounted display assembly 200.

Figure 3:
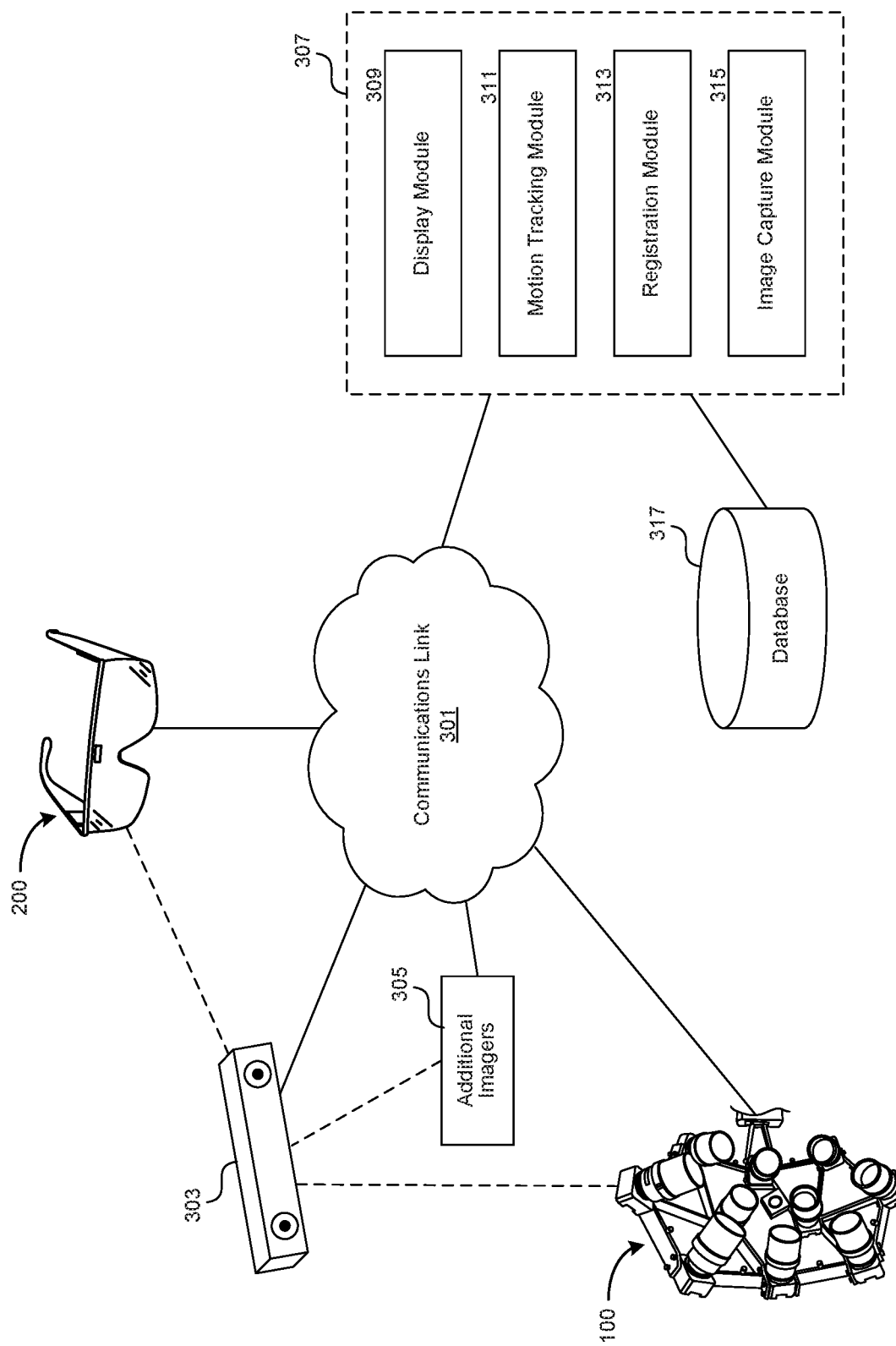
FIG. 3 is a schematic representation of a mediated-reality visualization system configured in accordance with an embodiment of the present technology.

FIG. 3 is a schematic representation of a mediated-reality visualization system configured in accordance with an embodiment of the present technology. The system includes a number of components in communication with one another via a communication link 301, which can be, for example, a public internet, private network such as an intranet, or other network. Connection between each component and the communication link 301 can be wireless (e.g., WiFi, Bluetooth, NFC, GSM, cellular communication such as CDMA, 3G, or 4G, etc.) or wired (e.g., Ethernet, FireWire cable, USB cable, etc.). The head-mounted display assembly 200 and the imaging assembly 100 are each coupled to the communication link 301. In some embodiments, the imaging assembly 100 can be configured to capture image data and the head-mounted display assembly 200 can be configured to display images to a user wearing the display assembly 200 via integrated display device 209. The display assembly 200 additionally includes a fiducial marker 217 that can be tracked by a tracker 303. The tracker 303 can determine the position and movement of the fiducial marker 217 via optical tracking, sonic or electromagnetic detection, or any other suitable approach to position tracking. The imaging assembly 100 can likewise include one or more fiducial markers that are tracked by the tracker 303. In some embodiments, the tracker 303 can be configured to use during surgery to track the position of the patient and certain anatomical features. For example, the tracker 303 can be part of a surgical navigation system such as Medtronic's StealthStation® surgical navigation system. Such systems can identify the position of probes around the surgical site and can also interface with other intraoperative imaging systems such as MRI, CT, fluoroscopy, etc. The tracker 303 can also track the position of additional imagers 305, for example, other cameras on articulated arms around the surgical site, endoscopes, cameras mounted on retractors, etc. For example, the additional imagers 305 can likewise be equipped with probes or fiducial markers to allow the tracker 303 to detect position and orientation. The position information obtained by the tracker 303 can be used to determine the position and orientation of the additional imagers 305 with respect to the display assembly 200 and with respect to the surgical site. In some embodiments, the additional imagers 305 can be selectively activated depending on the position and/or operation of the head-mounted display assembly 200. For example, when a user wearing the display assembly 200 is looking at a certain area that is within the field of view of an additional imager 305, that additional imager 305 can be activated and the data can be recorded for synthesis with image data from the display assembly 200. In some embodiments, the additional imagers 305 can be controlled to change their position and/or orientation depending on the position and/or operation of the head-mounted display assembly 200, for example by rotating an additional imager 305 to capture a field of view that overlaps with the field of view of the display assembly 200.

A computing component 307 includes a plurality of modules for interacting with the other components via communication link 301. The computing component 307 includes, for example, a display module 309, a motion tracking module 311, a registration module 313, and an image capture module 315. In some embodiments, the computing component 307 can include a processor such as a CPU which can perform operations in accordance with computer-executable instructions stored on a computer-readable medium. In some embodiments, the display module, motion tracking module, registration module, and image capture module may each be implemented in separate computing devices, each having a processor configured to perform operations. In some embodiments, two or more of these modules can be contained in a single computing device. The computing component 307 is also in communication with a database 317.

The display module 309 can be configured to provide display output information to the display assembly 200 for presentation to the user via the display device 209. As noted above, this can include stereoscopic display, in which different images are provided to each eye via first and second display devices 219a-b (FIG. 2B). The display output provided to the display assembly 200 can include a real-time or near-real-time feed of video captured by the imaging assembly 100. In some embodiments, the display output can include integration of other data, for example, pre-operative image data (e.g., CT, MRI, X-ray, fluoroscopy), standard anatomical images (e.g., textbook anatomical diagrams or cadaver-derived images), or current patient vital signs (e.g., EKG, EEG, SSEP, MEP). This additional data can be stored, for example, in the database 317 for access by the computing component 307. In some embodiments, additional real-time image data can be obtained from the additional imagers 305 and presented to a user via display device 209 of the display assembly 200 (e.g., real-time image data from other cameras on articulated arms around the surgical site, endoscopes, cameras mounted on retractors, etc.). Such additional data can be integrated for display; for example, it can be provided as a picture-in-picture or other overlay over the display of the real-time images from the imaging assembly 100. In some embodiments, the additional data can be integrated into the display of the real-time images from the imaging assembly 100; for example, X-ray data can be integrated into the display such that the user views both real-time images from the imaging assembly 100 and X-ray data together as a unified image. In order for the additional image data (e.g., X-ray, MRI, etc.) to be presented coherently with the real-time feed from the imaging assembly 100, the additional image data can be processed and manipulated based on the position and orientation of the display assembly 200. Similarly, in some embodiments textbook anatomical diagrams or other reference images (e.g., labeled images derived from cadavers) can be manipulated and warped so as to be correctly oriented onto the captured image. This can enable a surgeon, during operation, to visualize anatomical labels from preexisting images that are superimposed on top of real-time image data. In some embodiments, the user can toggle between different views via voice command, eye movement to select a menu item, assistant control, or other input. For example, a user can toggle between a real-time feed of images from the imaging assembly 100 and a real-time feed of images captured from one or more additional imagers 305.

The motion tracking module 311 can be configured to determine the position and orientation of the display assembly 200 and the imaging assembly 100 as well as any additional imagers 305, with respect to the surgical site. As noted above, the tracker 303 can track the position of the display assembly 200, the imaging assembly 100, and any additional imagers 305 optically or via other techniques. This position and orientation data can be used to provide appropriate display output via display module 309.

The registration module 313 can be configured to register all image data in the surgical frame. For example, position and orientation data for the display assembly 200, the plenoptic imaging assembly 100, and any additional imagers 305 can be received from the motion tracking module 311. Additional image data, for example, pre-operative images, can be received from the database 317 or from another source. The additional image data (e.g., X-ray, MRI, CT, fluoroscopy, anatomical diagrams, etc.) will typically not have been recorded from the perspective of either the display assembly 200, the imaging assembly 100, or of any of the additional imagers 305. As a result, the supplemental image data must be processed and manipulated to be presented to the user via display device 209 of the display assembly 200 with the appropriate perspective. The registration module 313 can register the supplemental image data in the surgical frame of reference by comparing anatomical or artificial fiducial markers as detected in the pre-operative images and those same anatomical or artificial fiducial markers as detected by the surgical navigation system, the display assembly 200, the imaging assembly 100, or other additional imagers 305.

The image capture module 315 can be configured to capture image data from the imaging assembly 100 and also from any additional imagers 305. The images captured can include continuous streaming video and/or still images. In some embodiments, one or more of the additional imagers 305 can be plenoptic cameras, in which case the image capture module 315 can be configured to receive the light field data and to process the data to render particular images.

Figure 4:
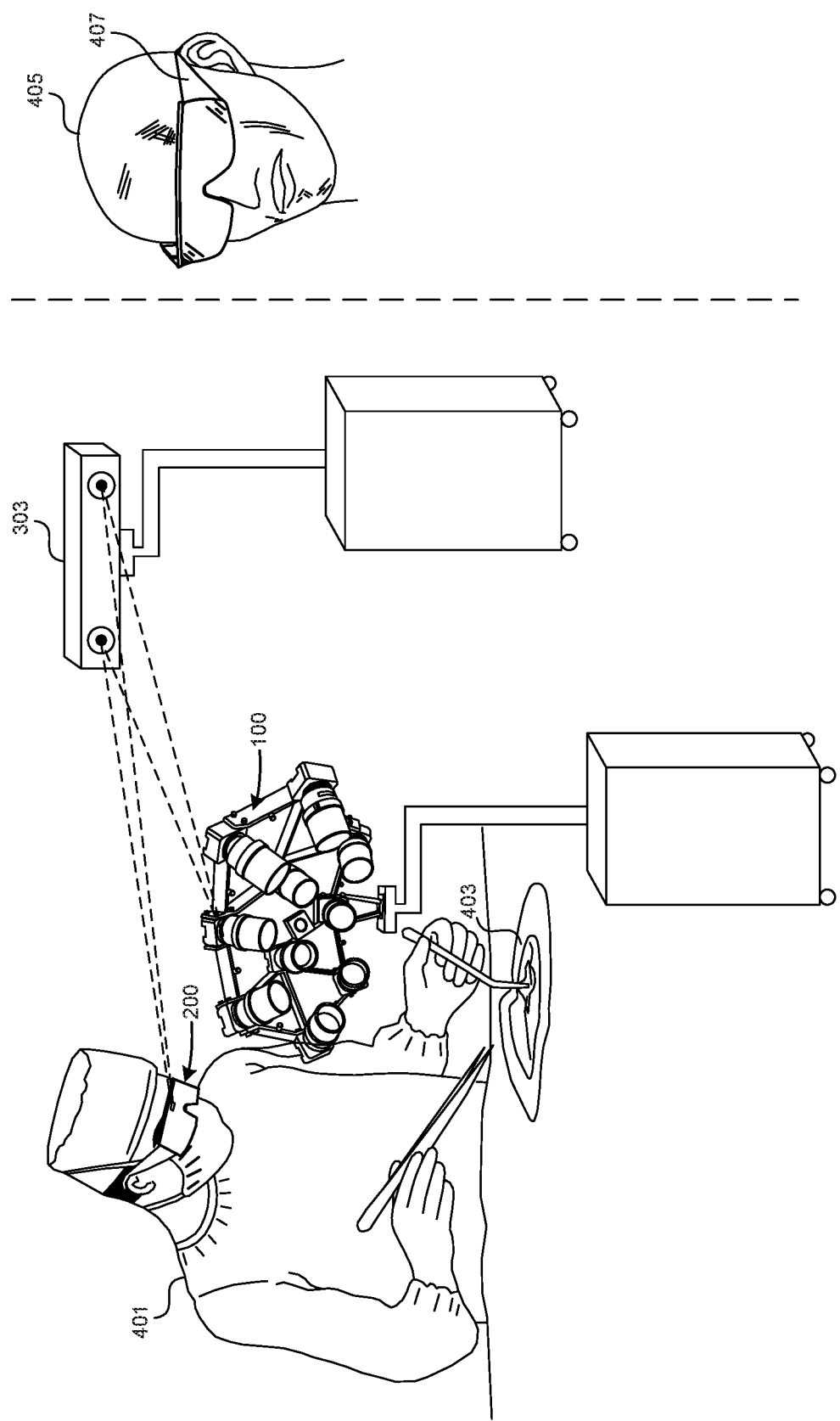
FIG. 4 illustrates a mediated-reality visualization system in use during a surgical procedure.

FIG. 4 illustrates a mediated-reality visualization system in operation during a surgical procedure. A surgeon 401 wears the head-mounted display assembly 200 during operation on a surgical site 403 of a patient. The imaging assembly 100 is mounted to an articulated arm to be positioned over the surgical site 403. The tracker 303 follows the movement and position of the display assembly 200 and the imaging assembly 100. As noted above, the tracker 303 can determine the position and movement of fiducial markers on the display assembly 200 and the imaging assembly 100 via optical tracking, sonic or electromagnetic detection, or any other suitable approach to position tracking. In some embodiments, the tracker 303 can be part of a surgical navigation system such as Medtronic's StealthStation® surgical navigation system. The tracker 303 can also track the position of additional imagers, for example, other cameras on articulated arms around the surgical site, endoscopes, cameras mounted on retractors, etc.

While the surgeon 401 is operating, images captured via the imaging assembly 100 are processed and displayed stereoscopically to the surgeon via an integrated display device 209 (FIG. 2B) within the display assembly 200. The result is a mediated-reality representation of the surgeon's field of view or any other desired view generated from the data captured by the imaging assembly 100. As noted above, additional image data or other data can be integrated and displayed to the surgeon as well. The display data being presented to the surgeon 401 can be streamed to a remote user 405, either simultaneously in real time or at a time delay. The remote user 405 can likewise don a head-mounted display assembly 407 configured with integrated stereoscopic display, or the display data can be presented to the remote user 405 via an external display. In some embodiments, the remote user 405 can control a surgical robot remotely, allowing telesurgery to be performed while providing the remote user 405 with the sense of presence and perspective to improve the surgical visualization. In some embodiments, multiple remote users can simultaneously view the surgical site from different viewpoints as rendered from multiple different plenoptic cameras and other imaging devices disposed around the surgical site.

The imaging assembly 100 and/or display assembly 200 may respond to voice commands or even track the surgeon's eyes-thus enabling the surgeon 401 to switch between feeds and tweak the level of magnification being employed. A heads-up display with the patient's vital signs (EKG, EEG, SSEPs, MEPs), imaging (CT, MRI, etc.), and any other information the surgeon desires may scroll at the surgeon's request, eliminating the need to interrupt the flow of the operation to assess external monitors or query the anesthesia team. Wireless networking may infuse the imaging assembly 100 and/or the display assembly 200 with the ability to communicate with processors (e.g., the computing component 307) that can augment the visual work environment for the surgeon with everything from simple tools like autofocus to fluorescence video angiography and tumor "paint." The imaging assembly 100 and display assembly 200 can replace the need for expensive surgical microscopes and even the remote robotic workstations of the near future-presenting an economical alternative to the current system of "bespoke" glass loupes used in conjunction with microscopes and endoscopes.

The head-mounted display assembly 200 can aggregate multiple streams of visual information and send it not just to the surgeon for visualization, but to remote processing power (e.g., the computing component 307 (FIG. 3)) for real-time analysis and modification. In some embodiments, the system can utilize pattern recognition to assist in identification of anatomical structures and sources of bleeding requiring attention, thus acting as a digital surgical assistant. Real-time overlay of textbook or adaptive anatomy may assist in identifying structures and/or act as a teaching aid to resident physicians and other learners. In some embodiments, the system can be equipped with additional technology for interacting with the surgical field; for example, the imaging assembly 100 can include LiDAR that may assist in analyzing tissue properties or mapping the surgical field in real time, thus assisting the surgeon in making decisions about the extent of resection, etc. In some embodiments, the light sources 105 integrated into the imaging assembly 100 can be "taught" (e.g., via machine-learning techniques) how to best illuminate certain operative situations or provide a different wavelength of light to interact with bio-fluorescent agents.

In some embodiments, the data recorded from the imaging assembly 100 and other imagers can be used to later generate different viewpoints and visualizations of the surgical site. For example, for later playback of the recorded data, an image having a different magnification, different integration of additional image data, and/or a different point of view can be generated. This can be particularly useful for review of the procedure or for training purposes.

In some embodiments, the position of external tools can be tracked for input. For example, the tip of a scalpel or other surgical tool can be tracked (e.g., using the tracker 303), and the enlarged volume can be located at the tip of the scalpel or other surgical tool. In some embodiments, the surgical tool can include haptic feedback or physical controls for the system or other surgical systems. In situations in which surgical tools are controlled electronically or electromechanically (e.g., during telesurgery where the tools are controlled with a surgical robot), the controls for those tools can be modified depending on the visualization mode. For example, when the tool is disposed inside the physical volume to be visually transformed (e.g., enlarged), the controls for the tool can be modified to compensate for the visual scaling, rotation, etc. This allows for the controls to remain the same inside the visually transformed view and the surrounding view. This modification of the tool control can aid surgeons during remote operation to better control the tools even as visualization of the tools and the surgical site are modified.

Information from additional cameras in the environment located close to points of interest can be fused with images from the imagers coupled to the head-mounted display, thereby improving the ability to enlarge regions of interest. Depth information can be generated or gained from a depth sensor and used to bring the entirety of the scene into focus by co-locating the focal plane with the physical geometry of the scene. As with other mediated reality, data can be rendered and visualized in the environment. The use of light-field capture and rendering can allow for viewing around occlusions and can remove specular reflections. In some embodiments, processing of light fields can also be used to increase the contrast between tissue types.

Although the example illustrated in FIG. 4 involves surgery, embodiments of the present technology can be usefully applied in a variety of fields. For example, a mediated-reality visualization system including a plenoptic imaging assembly and a head-mounted display assembly can be used in construction, manufacturing, the service industry, gaming, entertainment, and a variety of other contexts in which enhanced visualization is beneficial.

Figure 5:
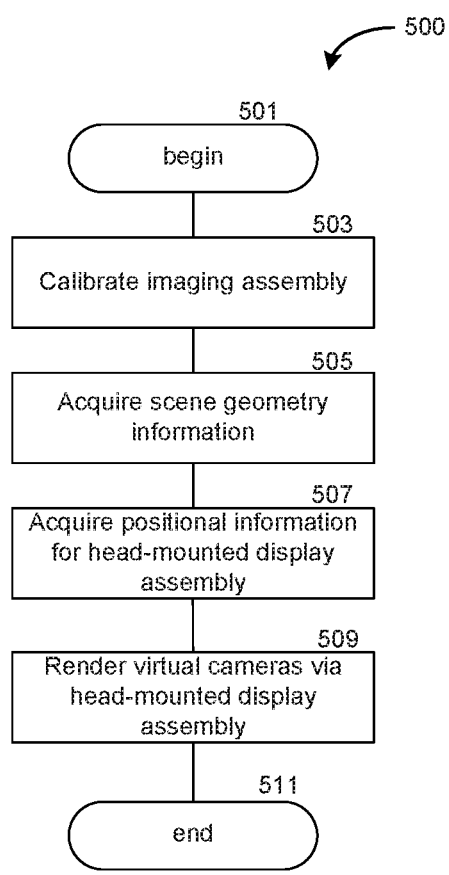
FIG. 5 is a block diagram of a method for capturing and rendering light fields to provide mediated-reality visualization according to one embodiment of the present technology.

FIG. 5 is a block diagram of a method for capturing and rendering light fields for enhanced visualization according to one embodiment of the present technology. The routine 500 begins in block 501. In block 503, the imaging assembly 100 is calibrated. The calibration can be performed by remote electronics (e.g., computing component 307) in wired or wireless communication with the imaging assembly 100 and/or the head-mounted display assembly 200. Or in some embodiments, the processing can be performed via control electronics 215a-b carried by the head-mounted display assembly 200. In some embodiments, the calibration and image processing steps can be performed by control electronics carried by the imaging assembly 100. Calibrating the imaging assembly 100 can include estimating the intrinsic parameters (i.e., lens model) of each imaging device 101 as well as estimating the extrinsic parameters (i.e., location and rotation in a global frame of reference, referred to herein as the "pose" of the device) of each imaging device 101. The estimated intrinsic parameters can be used to transform raw input images from an imaging device 101 into data identically generated from a perfect pinhole projective model, and usable in the techniques described below.

For each imaging device 101 in the array of the imaging assembly 100, the following intrinsic parameters may be estimated:
  (f), the focal length of the lens, expressed in pixels;
  (cx), the x-offset of the lens focal center from the image center, and
  (cy), the y-offset of the lens focal center from the image center.

A set of parameters for correcting lens distortion effects can also be estimated. Lens distortion causes straight lines in the world, which perspective projection projects as straight lines in an image, to appear curved, for example, the fish-eye effect.

When combined with camera pose, the above parameters provide sufficient information for a pinhole camera model with lens distortion. The pinhole model can be used to project points in the world onto pixels on the camera's image sensor, and likewise to project image pixels as rays in the world. Noise in the input images and a non-linear optimization criteria may mean that multiple images are required to achieve acceptable calibration accuracy. For digital cameras, image noise can come from several sources:

Sensor noise: The camera sensor itself adds random offsets from the "true" value due to thermal and quantum effects (smearing, blooming, diffusion, transfer efficiency, dynamic range).

Quantization: The fact that a continuous signal is being quantized both in space and in value prevent exact localization of image features.

Optical: Optical effects such as imperfect focus, as well as chromatic aberration confound precisely identifying features in the image on a per-pixel level.

After obtaining the calibration parameters for each imaging device 101 in the imaging assembly 100, the poses can be estimated with respect to each other, where pose includes both location and rotation information with respect to a reference coordinate frame. Accurate pose information can then be used for geometry acquisition and light-field rendering, as described in more detail below. Pose information and imaging device calibration can be particularly useful for light-field rendering because the renderer assumes having precise spatial coordinates and directions for each ray of light captured by the imaging devices 101 in the array. If a device's calibration and pose estimates are off by even a pixel, then the final image may incorporate image from adjacent spatial regions, leading to a blurring effect. Accordingly, accurate calibration and post information can be beneficial in achieving a sharp image.

In some embodiments, a known fiducial marker can be imaged by the imaging assembly 100 and used to estimate the pose of each imaging device. For example the ArUco library can be used for detection of square fiducial markers, as implemented in OpenCV. When detecting a marker of known physical size, and given accurate device calibration parameters, ArUco will provide the pose of the device with respect to the fiducial marker. Again, due to sensor noise in the imaging devices, there may a degree of uncertainty in the computed pose. In some embodiments, a known array of fiducial markers can be used to increase the accuracy of the pose estimation. The noise in the computed pose can be further reduced by averaging over several separate pose estimates, for example using nonlinear pose estimation.

Once the pose and device calibration parameters have been estimated, the routine 500 continues in block 505 with acquiring scene geometry information. As mentioned, light-field rendering using a sparse imaging device array benefits from a reasonably good estimate of the scene geometry. In some embodiments, the scene geometry can be estimated using a structured light technique, for example one based on a version of the 3DUNDERWORLD-SLS method as implemented in OpenCV. The basic principle of geometry reconstruction using stereo imaging device pairs is triangulation. Assuming the imaging devices are calibrated and their poses are known with respect to some coordinate system, then for each pixel in an image, a ray can be projected into the world, starting at the center of the imaging device and passing through that pixel. If the same world point is seen by both imaging devices, and the corresponding pixels that point is imaged by are known, then it is a simple matter to find the intersection of the rays to locate the point in the world.

Complications implementing such triangulation arise in the real world. A first problem involves determining which pixel in imaging device B represents the same world point as a particular pixel in imaging device A. A second problem is due to uncertainty from sensor noise and quantization effects. Even with sub-pixel accuracy, sensor noise may prevents perfect mapping between pixels of different imaging devices. As such, the projected rays from point correspondences may not actually intersect.

Structured light solves the correspondence problem by projecting a known pattern in to the scene. For example, the projector 107 integrated into the imaging assembly 100 can be used to project a known pattern into the field of view of the imaging devices 101. In one embodiment, the projected light forms a 1-dimensional binary gray code, first in the horizontal, then vertical directions. Thus, each imaging device image pixel can be uniquely associated with a source pixel of the projector 107. In some embodiments, this routine includes collecting a number of images corresponding to 2 log 2 (projector resolution)+2 images for geometry capture, for example 44 images in the case of a projector with a 1280×800 resolution.

Structured light correspondence may still not achieve perfect geometry capture. Since the resolution of each imaging device 101 can be higher than the effective imaged resolution of the projector 107, each projector pixel fills up multiple pixels of each imaging device 101. For the (re) projection steps described below, the average sub-pixel coordinate in the image captured by the imaging device 101 can be used. There may, however, be regions of missing information that are in full view of all imaging devices 101 and the projector 107 if the scene geometry is be oblique or reflective enough that insufficient light reaches the imaging devices 101 for decoding.

The close-but-not-intersecting problem can be solved by finding that point which is closest to all projected rays with respect to the sum of squared distances. In some embodiments, light-field rendering requires a continuous mesh without holes, while the output of the structured light system is a point cloud with missing information. In such embodiments, the missing information can be filled in as follows. Because triangulation can only be performed for world points that are seen by more than one imaging device 101 and are illuminated by the projector 107, each imaging device 101 captures a "shadow" from regions of non-convex geometry that are obscured from it. One way to fill in the blanks is to rotate the imaging devices 101 and projector 107 relative to the scene, however, this lengthens the capture time and requires an extra point cloud registration step. Alternatively, another imaging device 101 can be placed in such a way as to virtually "illuminate" the virtual shadows (and providing redundant information otherwise), leaving only the true shadow. Likewise, a second projector can provide information in the true shadow area. By using multiple imaging devices 101 in the array (e.g., using 10 imaging devices 101), the imaging assembly 100 captures redundant information across several viewing angles, leaving only any real shadow cast by the projector 107.

To create a dense mesh from the point cloud, the routine can perform the following steps:

1. Calibrate the projector: The decoded gray code directly associates each world point with a projector pixel. That correlation is used to estimate a rough calibration of the projector's intrinsics in the same way as calibrating an imaging device.
2. Create a sparse depth map: Project the point cloud onto a plane using calibration parameters from step 1, as though the projector were a camera viewing the point cloud.
3. Create a dense depth map: There will be holes in the projection due to slight misalignment between the calibration estimate and ground truth, as well as on regions that were not properly decoded. These holes can be filled by simply interpolating from nearby regions that have good data. While imperfect, this technique can be sufficient for light-field rendering applications. Although there may still be regions with missing data, there will be a connected component of dense depth information.
4. Create the mesh: Each valid pixel from the dense depth map is a vertex in the mesh. The calibration parameters from step 1 can be used to project the pixels out to obtain vertex coordinates. Faces can be defined as triangles from the vertices of adjacent pixels.

Once the scene geometry information is captured as a mesh, the routine 500 continues in block 507, in which the head-mounted display assembly 200 is queried for position and virtual camera parameters. As noted above, the location of the head-mounted display assembly 200 can be tracked via tracker 303. First and second eye trackers 221a-b can be used to determine the inter-pupillary distance (IPD) of a user and the virtual cameras can be positioned accordingly. In block 509, a stereoscopic view from the virtual cameras are rendered via the head-mounted display assembly 200. The view from the virtual cameras can use a weighted blend of the imaging devices 101 of the imaging assembly 100, as described in more detail below.

Figure 6:
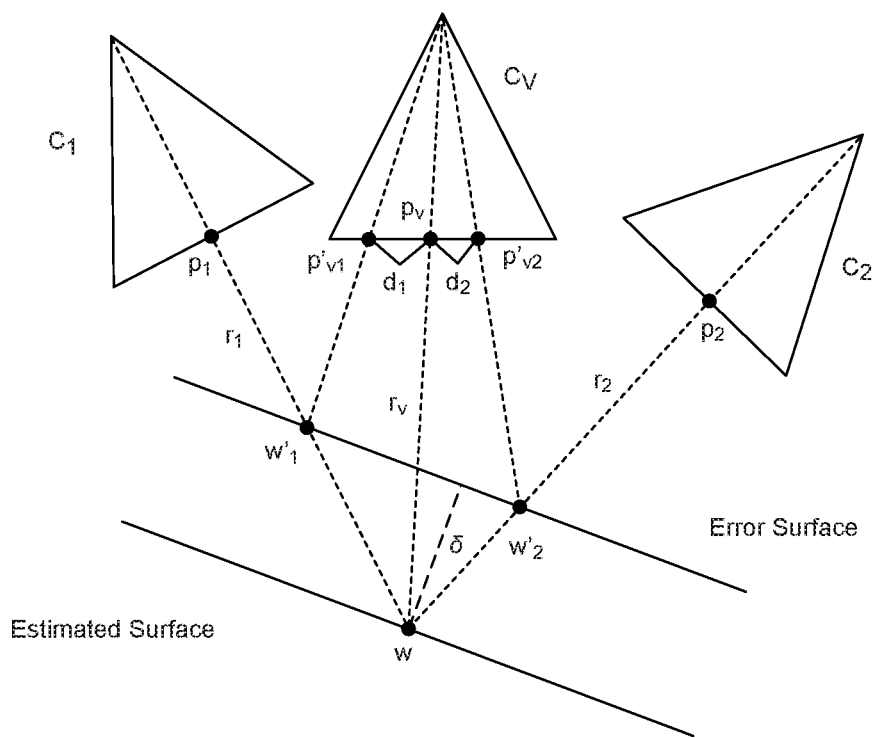
FIG. 6 is a schematic illustration of rendering a virtual camera using data from two real cameras.

FIG. 6 is a schematic illustration of rendering a virtual camera ($C_V$) based on light field data collected from two different physical imaging devices ($C_1$ and $C_2$). Light-field rendering includes synthesizing novel perspective views from a sampled light field, for example as captured via the imaging assembly 100. Associated with each camera $C_1$ and $C_2$ are values for the rotation, translation, and intrinsic parameters (focal length, distortion, etc.) If one had access to the continuous light field, then rendering a new view from a virtual camera $C_V$ would include, for each virtual pixel, sampling the light ray which would be projected through that pixel using the $C_V$'s camera model. The result is an image everywhere in perfect focus, a perfect pinhole rendering. However, in a sparse array of imaging devices, this approach is not possible.

Consider a single pixel $p_V$ on the imaging plane of $C_V$. Ignoring lens distortion, a ray $r_V$ can be projected into the world from the virtual camera $C_V$'s pinhole that passes through pixel $p_V$. The first object along $r_V$ is what would be imaged by the pixel $p_V$, were the virtual camera $C_V$ real. Assuming something to be imaged (e.g., a point on a surface) exists at a point w along the ray $r_V$, then any real cameras (e.g., camera C1 or C2) can be queried if they had point ω in their field of view for their pixel value $p_i$. For example, pixel p1 of real camera C1 images point w along ray $r_1$, and pixel p2 of real camera C2 also images point w along ray $r_2$. The set of all points ω for each virtual pixel form a focal surface, which is a height map from the perspective of $C_V$.

If N real cameras image point w, then a scheme is needed to assign a value for a virtual pixel $p_V$ that images point ω based on the data collected from the N real cameras. In some embodiments, the routine can use a weighted blend of the pixel values $p_i$s where the weight for a given pixel $p_i$ is a function of the angular distance between the virtual ray $r_V$ and the ray of the corresponding real camera $r_i$, and the angular distance between the surface normal at point w and virtual ray $r_V$. The focal surface for the virtual camera $C_V$ can be assumed to be closely coincident with the scene geometry acquired previously in block 505. Weights can then be assigned based on sensitivity analysis. In one embodiment, the sensitivity analysis can include the following steps:

1. For a virtual pixel $p_V$, find the intersection of its ray $r_V$ with the focal surface at point w, which lies on a locally approximated plane P (each pixel is treated separately, with its own focal plane).
2. For each real camera $C_i$, back project point w along corresponding ray $r_i$ to real pixel $p_i$.
3. Perturb the focal surface along its normal by an amount μ which represents uncertainty in the estimate of where the real geometry is located.
4. Find the intersection $ω'_i$ of $r_i$ with P+δμ.
5. Project $ω'_i$ into $C_V$ at sub-pixel location $p'_{V_i}$.
6. Let $di = \|p_V - p'_{V_i}\|_2$ be the sensitivity disparity for $C_i$.
7. Choose $l_i = v f_i(d_i)$ as the weight for $p_i$ for some function $f_i(d)$ and normalizing factor v so the weights sum to 1.

Repeat steps 1-7 for each virtual pixel $p_V$. In the example shown in FIG. 6, real pixel $p_2$ would receive a greater weight than real pixel $p_1$ (d2<d1) since ray $r_2$ is closer to the surface normal than ray $r_1$ The function $f_i(d)$ can be similar to a radial basis function and can be chosen such that the normalized weights rapidly fall off and overwhelmingly prefer the ray with the lowest disparity. For example, a radial Hermite spline with a long constant tail can be used, with clamp weights for rays behind the surface to 0. The long tail ensures that there will be at least some rendered data, even when the best real ray has a very large angular distance to the virtual ray. Where the spline ends and the tail begins, the confidence threshold is a tunable parameter that can be set to accommodate different camera geometries—denser arrays afford lower confidence thresholds. In some embodiments, select regions of the rendered image can be artificially darkened where the sum of all weights is below a threshold to visually indicate a high level of uncertainty, while still providing the best guess at what the virtual camera should see.

This method for calculating the weights is an approximation to a probabilistic treatment of the light paths in the scene. This can assign high weight to those pixels $p_i$ that have a good chance of actually being projected to $p_V$ given the expected uncertainty. Pixels aren't single points, but instead integrate incoming light over a finite area. A more complete model can account for projecting each pixel's solid angle into the scene with some distribution over where it integrates light. The weights would reflect these projected probability distributions. In some embodiments, the approximation can be used for computational convenience.

The routine ends in block 511. The process outlined in blocks 503-509 can be repeated. Blocks 503 and 505 can be performed independently and in parallel at different frame rates as compared with blocks 507 and 509, due to the decoupling between light field capture and image display.

In some embodiments, specularity can be evaluated and subtracted using light-field rendering techniques. Specularities are the bright spots of directly reflected light that appear on shiny objects. If no accommodation is made for specularity, then when the virtual camera moves around, specularities captured by the real cameras will appear to fade in and out according to the pixel weights, rather than track across the surface as expected. To simulate authentic specular response, it is beneficial to determine: 1) the diffuse (matte) color properties of the surface, 2) the surface geometry, and 3) location of lights in the scene. As noted above, the surface geometry can be calculated as described with respect to block 505. Also, the imaging assembly 100 can be equipped with light sources 105 that are positioned at known locations with respect to the imaging devices 101. As such, the remaining property to be determined is the diffuse (matte) color properties of the surface. In some embodiments, these properties can be determined by modulating the on-off values of the light sources 105 with mutually orthogonal binary codes across a series of exposures, similar to the approach taken in code division multiple access schemes. The orthogonality of the codes allows a post processing step to separate the contribution of each light source 105, as well as of the ambient light, producing a stack (e.g., a stack of nine images in the case of an assembly with 8 light sources), each with only one light source activated (8 light sources in addition to the ambient conditions).

By examining the distribution of intensities on a per-pixel basis, the median values can be assigned as the diffuse value—the brightest value represents the likely presence of a specular highlight, and the darkest value represents the condition when that pixel is in shadow. By averaging over the median intensity values, the resulting image can remove nearly all the specular highlights. The variance in intensity for a pixel gives a good indication for how shiny the surface seen by that pixel is. Combined with estimated geometry and surface normals, this information allows simulation of moving specular highlights as the virtual camera position is moved with respect to the imaged surface.

Examples

1. A mediated-reality visualization system, comprising:
   a head-mounted display assembly comprising—
      a front side facing a first direction;
      a rear side opposite the front side and facing a second direction opposite the first, the rear side configured to face a user's face when worn by the user; and
      a stereoscopic display device facing the second direction, the stereoscopic display device comprising a first display and a second display, wherein, when the head-mounted display assembly is worn by the user, the first display is configured to display an image to a right eye of the user and the second display is configured to display an image to a left eye of the user; and
   an imaging assembly separate and spaced apart from the head-mounted display assembly, the imaging assembly configured to capture light-field data; and
   a computing device in communication with the stereoscopic display device and the imaging assembly, the computing device configured to—
      receive the light-field data from the imaging assembly;
      process the light-field data to render first and second virtual cameras; and
      present a real-time stereoscopic image via the stereoscopic display device by displaying an image from the first virtual camera at the first display and displaying an image from the second virtual camera at the second display.
2. The mediated-reality visualization system of example 1 wherein the imaging assembly comprises at least 8 imaging devices.
3. The mediated-reality visualization system of example 1 or 2 wherein the imaging assembly comprises a plenoptic camera.
4. The mediated-reality visualization system of any one of examples 1-3 wherein the imaging assembly is coupled to an articulated arm positionable over a working site.
5. The mediated-reality visualization system of any one of examples 1-4 wherein the first and second virtual cameras are rendered at positions corresponding to eye positions of a user of the head-mounted display assembly.
6. The mediated-reality visualization system of any one of examples 1-4 wherein the virtual cameras are rendered at positions different from the eye positions of a user of the head-mounted display assembly.
7. The mediated-reality visualization system any one of examples 1-6 wherein the image from the first virtual camera and the image from the second virtual camera each comprises a non-planar focal surface.
8. The mediated-reality visualization system of example 7 wherein focal surface corresponds to an estimated surface geometry of an imaged scene.
9. The mediated-reality visualization system of any one of examples 1-8 wherein the computing device is further configured to:
   receive auxiliary image data;
   process the auxiliary image data; and
   present a processed auxiliary image from the auxiliary image data at the first display and/or the second display.

10. The mediated-reality visualization system of example 9 wherein the auxiliary image data comprises at least one of: fluorescence image data, magnetic resonance imaging data, computed tomography image data, X-ray image data, anatomical diagram data, and vital-signs data.

11. The mediated-reality visualization system of any one of examples 1-10 wherein the computing device is further configured to present the real-time stereoscopic image to a second head-mounted display assembly.

12. The mediated-reality visualization system of example any one of examples 1-11 wherein the imaging assembly further comprises:
a plurality of separately controllable light sources configured to illuminate a scene to be imaged; and
a projector configured to project an image into the scene to be imaged.

13. A mediated-reality visualization system, comprising:
an imaging assembly configured to capture light-field data;
a head-mounted display assembly separate and spaced apart from the imaging assembly, the head-mounted display assembly comprising—
a frame configured to be worn on a user's head; and
a display device coupled to the frame, the display device configured to display an image towards an eye of the user;
a computing device in communication with the display device and the one or more imaging devices, the computing device configured to—
receive the light-field data from the imaging assembly;
render at least one virtual camera from the light-field data, and
present an image from the at least one virtual camera via the display device.

14. The mediated-reality visualization system of example 13, wherein the imaging assembly comprises at least one of: a plenoptic camera or at least eight cameras.

15. The mediated-reality visualization system of example 13 or 14 wherein the computing device is configured to render the at least one virtual camera at a location corresponding to a position of a user's eye when the frame is worn by the user.

16. The mediated-reality visualization system of any one of examples 13-15 wherein the computing device is configured to present the image in real time.

17. The mediated-reality visualization system of any one of examples 13-16 wherein the computing device is configured to render the at least one virtual camera by rendering an enlarged view of a portion of a captured light field.

18. A method for providing mediated-reality visualization, the method comprising:
capturing light-field data via an imaging assembly;
processing the light-field data to render at least one virtual camera; and
displaying an image from the virtual camera via a head-mounted display, wherein the head-mounted display is separate and spaced apart from the imaging assembly.

19. The method of example 18, further comprising:
processing the light-field data to render two virtual cameras: and
stereoscopically displaying images from the two virtual cameras via the head-mounted display.

20. The method of example 18 or 19 wherein rendering the at least one virtual camera comprises rendering the at least one virtual camera at a location corresponding to a position of an eye of a user when the display is mounted to the user's head.

21. The method of any one of examples 18-20, further comprising:
receiving auxiliary image data;
processing the auxiliary image data; and
displaying the auxiliary image data via the head-mounted display.

22. The method of any one of examples 18-21 wherein rendering the at least one virtual camera comprises rendering an enlarged view of a portion of a captured light field.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the invention have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method of imaging a physical scene, the method comprising:
receiving image data of the physical scene from a camera assembly having a plurality of cameras configured to capture the image data;
rendering a virtual camera;
generating an image from the virtual camera by determining a value for each of a plurality of virtual pixels in the image from the virtual camera, wherein determining the value for each of the plurality of virtual pixels comprises— determining a point in the physical scene corresponding to the virtual pixel along a virtual ray;

determining a first pixel in the image data from the first one of the cameras that images the point in the physical scene along a first ray;

determining a second pixel in the image data from the second one of the imaging devices that images the point in the physical scene along a second ray; and weighting a value of the first pixel and a value of the second pixel to determine a value of the virtual pixel based on (i) a first angular distance between the first ray and the virtual ray, (ii) a second angular distance between the second ray and the virtual ray, and (iii) a third angular distance between the virtual ray and a surface normal at the point in the physical scene; and displaying the image from the virtual camera at a display, wherein the camera assembly is separate and spaced apart from the display.

2. The method of claim 1 wherein the cameras are each directed toward and focused on a generally common point in the physical scene.

3. The method of claim 1 wherein the image data comprises light field image data.

4. The method of claim 1 wherein the method further comprises determining a surface geometry of the physical scene.

5. The method of claim 1 wherein the image from the virtual camera comprises a non-planar focal surface.

6. The method of claim 5 wherein the method further comprises determining a surface geometry of the physical scene, and wherein the non-planar focal surface corresponds to the determined surface geometry of the physical scene.

7. The method of claim 1 wherein the camera assembly comprises a rigid frame, and wherein the cameras are mounted to frame.

8. The method of claim 1 wherein the method further comprises continuously receiving the image data, processing the image data, generating the image from the virtual camera, and displaying the image from the virtual camera at the display.

9. The method of claim 1 wherein the camera assembly is coupled to an articulated arm positionable over the physical scene.

10. The method of claim 1 wherein the cameras each have a different perspective of the physical scene, and wherein the virtual camera has a perspective of the physical scene different from any of the cameras.

11. The method of claim 1 wherein the physical scene comprises a surgical scene.

12. The method of claim 1 wherein the method further comprises tracking a position of the camera assembly relative to the physical scene.

13. The method of claim 1 wherein the display is a head-mounted display.

14. A system for imaging a physical scene, the system comprising:

a camera assembly including a plurality of cameras configured to capture image data of the physical scene;

a computing device communicatively coupled to the camera assembly, wherein the computing device has a memory containing computer-executable instructions and a processor for executing the computer-executable instructions contained in the memory, and wherein the computer-executable instructions, when executed by the processor, cause the processor to— receive the image data from the camera assembly;

render a virtual camera; and generate an image from the virtual camera by determining a value for each of a plurality of virtual pixels in the image from the virtual camera, wherein determining the value for each of the plurality of virtual pixels comprises— determining a point in the physical scene corresponding to the virtual pixel along a virtual ray;

determining a first pixel in the image data from a first one of the cameras corresponding to the point in the physical scene along a first ray;

determining a second pixel in the image data from a second one of the cameras corresponding to the point in the physical scene along a second ray; and weighting a value of the first pixel and a value of the second pixel to determine a value of the virtual pixel based on (i) a first angular distance between the first ray and the virtual ray, (ii) a second angular distance between the second ray and the virtual ray, and (iii) a third angular distance between the virtual ray and a surface normal at the point in the physical scene; and a display communicatively coupled to the computing device, wherein the display is separate and spaced apart from the camera assembly, and wherein the display is configured to receive the image from the virtual camera from the computing device and display the image from the virtual camera.

15. The system of claim 14 wherein the cameras are each directed toward and focused on a generally common point in the physical scene.

16. The system of claim 15 wherein the camera assembly comprises a rigid frame, wherein the cameras are mounted to frame, and wherein the camera assembly is coupled to an articulated arm positionable over the physical scene.

17. The system of claim 14 wherein the cameras each have a different perspective of the physical scene, and wherein the virtual camera has a perspective of the physical scene different from any of the cameras.

18. The system of claim 14 wherein the physical scene comprises a surgical scene.

19. The system of claim 14 wherein the image data comprises light field image data.

20. The system of claim 14, further comprising a tracking device communicatively coupled to the computing device, wherein the tracking device is configured to track a position of the camera assembly relative to the physical scene.

* * * * *